(12) United States Patent
Miwa (10) Patent No.: US 9,770,572 B2
(45) Date of Patent: Sep. 26, 2017

(54) DEVICE, METHOD, MEDIUM FOR GUIDING A USER TO A DESIRED SLEEP STATE

(71) Applicant: Yamaha Corporation, Hamamatsu-shi, Shizuoka-Ken (JP)

(72) Inventor: Akihiro Miwa, Hamamatsu (JP)

(73) Assignee: Yamaha Corporation, Hamamatsu-shi (JP)

( * ) Notice: Subject to any disclaimer, the term of this patent is extended or adjusted under 35 U.S.C. 154(b) by 207 days.

(21) Appl. No.: 14/590,051

(22) Filed: Jan. 6, 2015

(65) Prior Publication Data

US 2015/0190609 A1 Jul. 9, 2015

(30) Foreign Application Priority Data

Jan. 8, 2014 (JP) ................................ 2014-001821
Nov. 19, 2014 (JP) ................................ 2014-234382

(51) Int. Cl.
*A61M 21/02* (2006.01)
*A61B 5/00* (2006.01)
*A61M 21/00* (2006.01)

(52) U.S. Cl.
CPC ........... *A61M 21/02* (2013.01); *A61B 5/4812* (2013.01); *A61B 5/4815* (2013.01); *A61B 5/4836* (2013.01); *A61M 2021/0027* (2013.01); *A61M 2205/3375* (2013.01)

(58) Field of Classification Search
CPC ... A61B 5/4812; A61B 5/4815; A61B 5/4836; A61M 2205/3375; A61M 2021/0027; A61M 21/02
See application file for complete search history.

(56) References Cited

U.S. PATENT DOCUMENTS

| 2007/0083079 | A1* | 4/2007 | Lee ..................... A61B 5/4806 600/27 |
| 2011/0319721 | A1 | 12/2011 | Hamaguchi |
| 2013/0181841 | A1 | 7/2013 | Iizuka |
| 2013/0190556 | A1* | 7/2013 | Wetmore ............... G09B 19/00 600/28 |

(Continued)

FOREIGN PATENT DOCUMENTS

| EP | 1 886 707 A1 | 2/2008 |
| EP | 2 495 005 A1 | 9/2012 |
| JP | 2012-65996 A | 4/2012 |

OTHER PUBLICATIONS

Eberhardt J et al. "The influence of continuous and intermittent traffic noise on sleep". Journal of Sound and Vibration. vol. 116, No. 3, Aug. 8, 1987.*

(Continued)

*Primary Examiner* — Christine H Matthews
*Assistant Examiner* — Joshua D Lannu
(74) *Attorney, Agent, or Firm* — Crowell & Moring LLP (57) ABSTRACT

A device includes a sleep depth data acquisition unit configured to acquire sleep depth data indicating a sleep depth of a user in a state in which a sound is being emitted. The device also includes a generation unit configured to generate influence data indicating an influence exerted on a variation with time of the sleep depth of the user by the sound based on a variation with time of the sleep depth indicated by the sleep depth data acquired by the sleep depth data acquisition unit and a variation with time of the sleep depth serving as a reference relating to the user.

5 Claims, 7 Drawing Sheets

(56) References Cited

U.S. PATENT DOCUMENTS

2013/0234823 A1* 9/2013 Kahn .................... A61M 21/02
340/3.1

OTHER PUBLICATIONS

European Search Report dated Jun. 2, 2015 (six (6) pages).
J. L. Eberhardt, et al., "The Influence of Continuous and Intermittent Traffic Noise on Sleep", Journal of Sound and Vibration, 1987, vol. 116, No. 3, pp. 445-464, London, GB.
Musa H. Asyali, et al., "Determining a continuous marker for sleep depth", Computers in Biology and Medicine, 2007, vol. 37, No. 11, pp. 1600-1609, New York, NY, US.
English-Language Office Action issued in counterpart European Application No. 15 150 277.0 dated Jun. 7, 2017 (5 pages).
Chen et al., "Sedative Music Facilitates Deep Sleep in Young Adults", Journal of Alternative and Complementary Medicine, 2014, pp. 312-317, vol. 20, No. 4, XP055377473.

* cited by examiner

| SOUND DATA FILE NAME | INFLUENCE DATA | |
|---|---|---|
| | DEEPENING FLAG | MAINTAINING FLAG |
| ... | ... | ... |
| ... | ... | ... |
| ... | ... | ... |

| SOUND DATA FILE NAME | START TIME | END TIME |
|---|---|---|
| ... | ... | ... |
| ... | ... | ... |
| ... | ... | ... |

FIG.5

| TIME | SLEEP DEPTH |
|------|-------------|
| ... | ... |
| ... | ... |
| ... | ... |

| PRESENCE/ ABSENCE OF SOUND EMISSION | SLEEP DEPTH IN STABLE STAGE | TIME LENGTH OF STABLE STAGE |
|---|---|---|
| NON-SOUND EMITTING DAY | ... | ... |
| | ... | ... |
| | ... | ... |
| | ... | ... |
| | ... | ... |
| | ... | ... |
| | ... | ... |
| | ... | ... |
| EXAMINATION SOUND EMITTING DAY | ... | ... |
| | ... | ... |
| | ... | ... |
| | ... | ... |
| | ... | ... |
| | ... | ... |
| | ... | ... |

| DISTURBANCE SOUND ID | ACOUSTIC CHARAC-TERISTIC | DISTURBANCE SOUND DATA FILE NAME | INFLUENCE DATA | |
|---|---|---|---|---|
| | | | DEEPENING FLAG | MAINTAINING FLAG |
| ... | ... | ... | ... | ... |
| ... | ... | ... | ... | ... |
| ... | ... | ... | ... | ... |

FIG.12

| DISTURBANCE SOUND ID | START TIME | END TIME |
|---|---|---|
| ... | ... | ... |
| ... | ... | ... |
| ... | ... | ... |

FIG.13

DEVICE, METHOD, MEDIUM FOR GUIDING A USER TO A DESIRED SLEEP STATE

CROSS-REFERENCE TO RELATED APPLICATION

The present application claims priority from Japanese applications JP2014-234382 and JP2014-001821, the content of which is hereby incorporated by reference into this application.

BACKGROUND OF THE INVENTION

1. Field of the Invention

The present invention relates to a technology of guiding a user to a desired sleep state.

2. Description of the Related Art

There is proposed a technology of guiding a user to a desired sleep state. For example, a sleep device disclosed in Japanese Patent Application Laid-open No. 2012-65996 guides a subject person to a desired sleep state by measuring a current sleep depth of the subject person and giving the subject person a stimulus corresponding to a degree of discrepancy between the measured sleep depth and a target sleep depth.

SUMMARY OF THE INVENTION

In general, it is said that natural sounds or the like that gradually change such as sounds of falling rain or rippling waves are sounds that guide the sleeping person to a good sleep. However, it is assumed that the sound that guides the sleeping person to a good sleep differs depending on the person. Up to now, there is no way to know the sound that guides each individual person to a good sleep during his/her sleep. It is an object of one or more embodiments of the present invention to provide a device for identifying the sound that guides each individual person to a good sleep during his/her sleep.

In one or more embodiments of the present invention, a device includes a sleep depth data acquisition unit configured to acquire sleep depth data indicating a sleep depth of a user in a state in which a sound is being emitted. The device also includes a generation unit configured to generate influence data indicating an influence exerted on a variation with time of the sleep depth of the user by the sound based on a variation with time of the sleep depth indicated by the sleep depth data acquired by the sleep depth data acquisition unit and a variation with time of the sleep depth serving as a reference relating to the user.

In one or more embodiments of the present invention, a device includes a sleep state data acquisition unit configured to acquire sleep state data indicating a current sleep state of a user, and a selection unit configured to select at least one piece of sound data from among a plurality of pieces of sound data based on the sleep state data and a plurality of pieces of influence data. The plurality of pieces of influence data are respectively associated with the plurality of pieces of sound data. Each of the plurality of pieces of influence data indicates an influence exerted on a variation with time of a sleep depth by each of sounds indicated by the plurality of pieces of sound data.

In one or more embodiments of the present invention, a non-transitory computer-readable storage medium holding a program comprising instructions for acquiring sleep depth data indicating a sleep depth of a user in a state in which a sound is being emitted, and generating influence data indicating an influence exerted on a variation with time of the sleep depth of the user by the sound based on a variation with time of the sleep depth indicated by the sleep depth data and a variation with time of the sleep depth serving as a reference relating to the user.

According to one or more embodiments of the present invention, it is identified which of a plurality of sounds is a sound that guides a sleeping person to a good sleep.

DETAILED DESCRIPTION OF THE INVENTION

1. Embodiment

Now, a description is made of a good sleep sound reproduction system 1 according to an embodiment of the present invention with reference to the accompanying drawings. The good sleep sound reproduction system 1 is a system for emitting a sound (hereinafter referred to as "good sleep sound") that guides a user U to a good sleep while the user U is sleeping.

Figure 1:
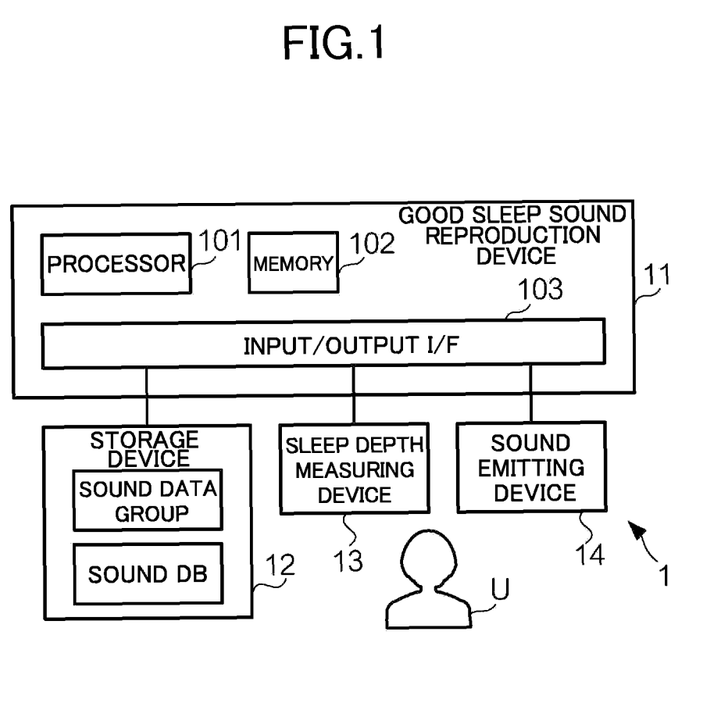
FIG. 1 is a block diagram illustrating a configuration of a good sleep sound reproduction system according to an embodiment of the present invention.

FIG. 1 is a block diagram illustrating a configuration of the good sleep sound reproduction system 1. The good sleep sound reproduction system 1 includes a good sleep sound reproduction device 11 for examining the good sleep sound for the user U and causing a sound emitting device to emit the examined good sleep sound, a storage device 12 for storing a plurality of sound data pieces (sound data group) indicating a sound to be a candidate for the good sleep sound and a sound DB serving as a database for managing the sound data group, a sleep depth measuring device 13 for measuring the sleep depth of the user U and outputting sleep depth data indicating a measurement result, and a sound emitting device 14 for emitting a sound in accordance with the sound data. The storage device 12, the sleep depth measuring device 13, and the sound emitting device 14 are connected to the good sleep sound reproduction device 11. Note that, those devices may be connected to one another in any one of a wired manner or a wireless manner, may be connected directly to one another, or may be connected to one another through a network. Further, in the case of being connected directly to one another, the storage device 12, the sleep depth measuring device 13, and the sound emitting device 14 may each be connected to the good sleep sound reproduction device 11 as an external device, or may be built therein.

The good sleep sound reproduction device 11 includes a processor 101 for performing various arithmetic operations in accordance with an OS, application programs, and the like and controlling other components, a memory 102 for storing the above-mentioned programs and various kinds of data, and an input/output I/F 103 serving as an interface for inputting/outputting the various kinds of data to/from the external devices (storage device 12, sleep depth measuring device 13, and sound emitting device 14).

The storage device 12 is a known storage device including a hard disk drive, a solid-state drive (SSD), or the like. The sleep depth measuring device 13 is a known sleep meter, for example, a meter for measuring a depth of a sleep based on sensing results of an electroencephalogram, a pulse, a heartbeat, respiration, a body motion, and the like of the user U, but a method therefor is arbitrary. Note that, in the following description, the sleep depth measuring device 13 is configured to generate and output the sleep depth data indicating the sleep depth by, for example, an integer of anyone of 0 to 4 (indicating the deeper sleep depth as the numerical value becomes larger). The sound emitting device 14 is a known speaker, and includes an amplifier or the like as necessary.

Figure 2:
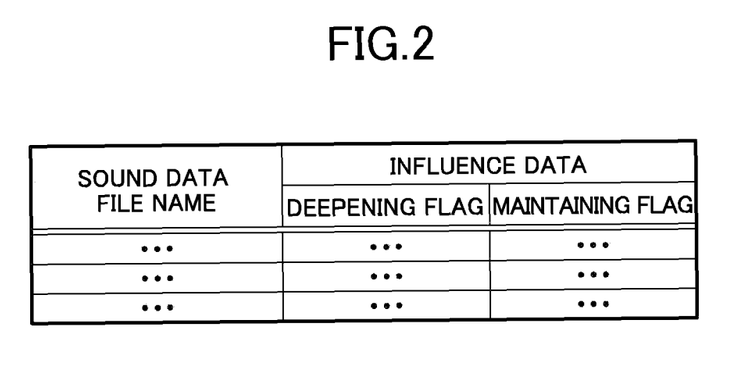
FIG. 2 is a table exemplifying a data structure of a sound DB for managing sound data according to the embodiment.

FIG. 2 is a table exemplifying a data structure of the sound DB stored in the storage device 12. The sound DB includes a data record corresponding to each of sound data pieces stored in the storage device 12, and each data record includes data indicating a file name of the sound data (identification information on the sound data) and influence data. The influence data indicates an influence exerted on the sleep depth of the user U by a sound indicated by the sound data. In this embodiment, as an example, the influence data is formed of two data pieces, in other words, a deepening flag and a maintaining flag. The deepening flag indicates whether or not the sound indicated by the sound data is a sound that deepens the sleep depth of the user U. Further, the maintaining flag indicates whether or not the sound indicated by the sound data is a sound that maintains the sleep depth when the sleep depth of the user U is stabilized at a deep level. The influence data is generated in an operation (examination mode) of the good sleep sound reproduction device 11 described later, and is stored in the storage device 12. Note that, usage of the deepening flag and the maintaining flag is described later.

The sound data stored in the storage device 12 may indicate any sound, but it is desired that the sound include white noise, sounds of rippling waves, and calm music that are unlikely to inhibit the sleep of the user U. Further, the sound data stored in the storage device 12 may be added by a user.

The operation of the good sleep sound reproduction system 1 is distinguished into a mode (hereinafter referred to as "examination mode") for examining the good sleep sound for the user U and a mode (hereinafter referred to as "operation mode") for emitting the examined good sleep sound to the user U.

1.1. Examination Mode

Figure 3:
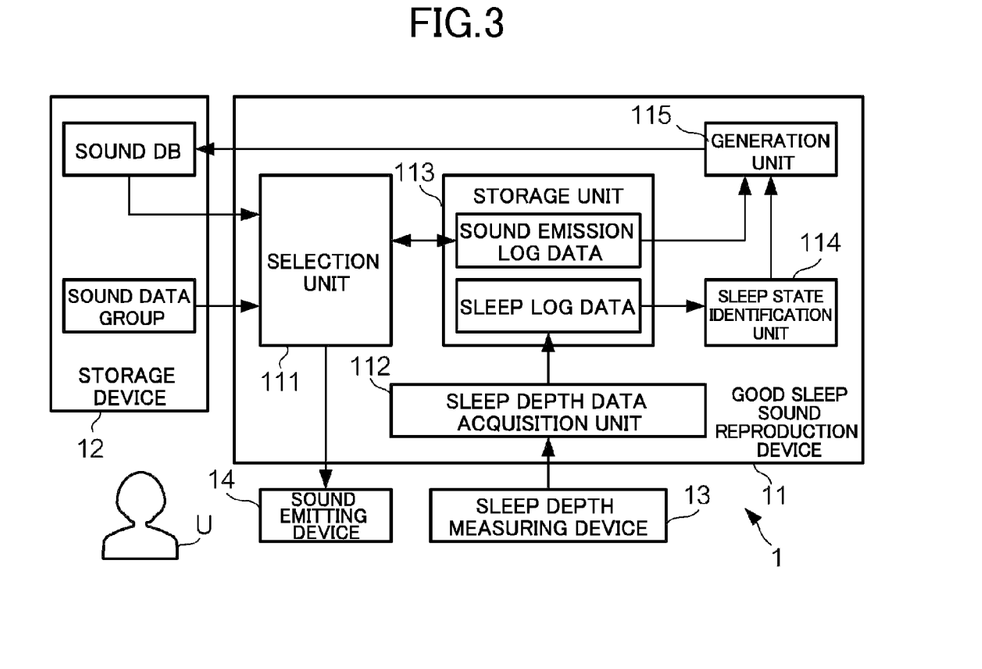
FIG. 3 is a block diagram for illustrating a functional configuration (examination mode) of a good sleep sound reproduction device according to the embodiment.

The processor 101 of the good sleep sound reproduction device 11 operates as a device including a functional configuration illustrated in FIG. 3 by performing processing in accordance with a program for the examination mode stored in the memory 102.

In the examination mode, the good sleep sound reproduction device 11 includes, as the functional configuration, a selection unit ill, a sleep depth data acquisition unit 112, a storage unit 113, a sleep state identification unit 114, and a generation unit 115. The sleep state identification unit 114 may be a part of the generation unit 115. Each of those components is described below.

When the good sleep sound reproduction device 11 starts an operation for the examination mode, the selection unit 111 selects the sound data for examination from the sound data group stored in the storage device 12. The selection unit 111 may select the sound data for examination at random, or may select the sound data for examination in accordance with a predetermined rule, for example, may select preferentially the sound data indicating a sound to be the good sleep sound for most users.

After that, when the present day is a day on which the sound for the examination is to be emitted, in accordance with a predetermined operation performed for the good sleep sound reproduction device 11 by the user U at a time of retiring to bed, the selection unit 111 reads the selected sound data for examination from the storage device 12, and repeatedly outputs the read sound data to the sound emitting device 14, to thereby cause the sound emitting device 14 to perform loop playback of the sound. When the sound data is being output to the sound emitting device 14, the selection unit 111 stops the output in accordance with a predetermined operation performed for the good sleep sound reproduction device 11 by the user U at a time of awaking.

In order to statistically identify an influence exerted on the sleep depth of the user U by a sound (hereinafter referred to as "examination sound") indicated by one piece of sound data for examination, the selection unit 111 alternately provides a day (hereinafter referred to as "non-sound emitting day") on which the sound emitting device 14 is not caused to emit the examination sound and a day (hereinafter referred to as "examination sound emitting day") on which the sound emitting device 14 is caused to emit the examination sound. However, units of a period during which the sound emitting device 14 is caused to emit the examination sound by the selection unit 111 and a period during which the sound emitting device 14 is not caused to emit the examination sound thereby are not limited to units of days, and, for example, 1.5 hours (time period required for one unit of a sleep cycle of most people) may be employed as the units.

Figure 4:
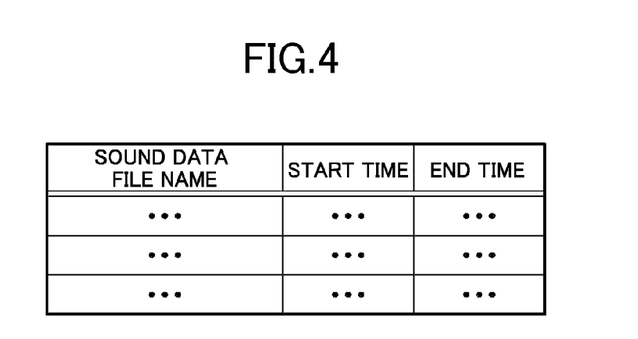
FIG. 4 is a table exemplifying a structure of sound emission log data according to the embodiment.

The selection unit 111 generates the file name (sound data file name) of the sound data output to the sound emitting device 14 and sound emission log data indicating a start time and an end time of the output, and stores the sound data file name and the sound emission log data in the storage unit 113. FIG. 4 is a table exemplifying a structure of the sound emission log data.

The sleep depth data acquisition unit 112 acquires the sleep depth data sequentially output from the sleep depth measuring device 13 at predetermined time intervals. However, a timing at which the sleep depth measuring device 13 outputs the sleep depth data and a timing at which the sleep depth data acquisition unit 112 acquires the sleep depth data are not limited to the predetermined time intervals, and, for example, the sleep depth data acquisition unit 112 may be configured to acquire the sleep depth data output from the sleep depth measuring device 13 at a timing at which there is a change in the sleep depth of the user U.

Figure 5:
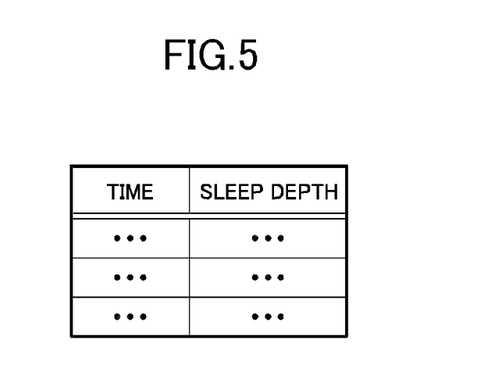
FIG. 5 is a table exemplifying a structure of sleep log data according to the embodiment.
Figure 6:
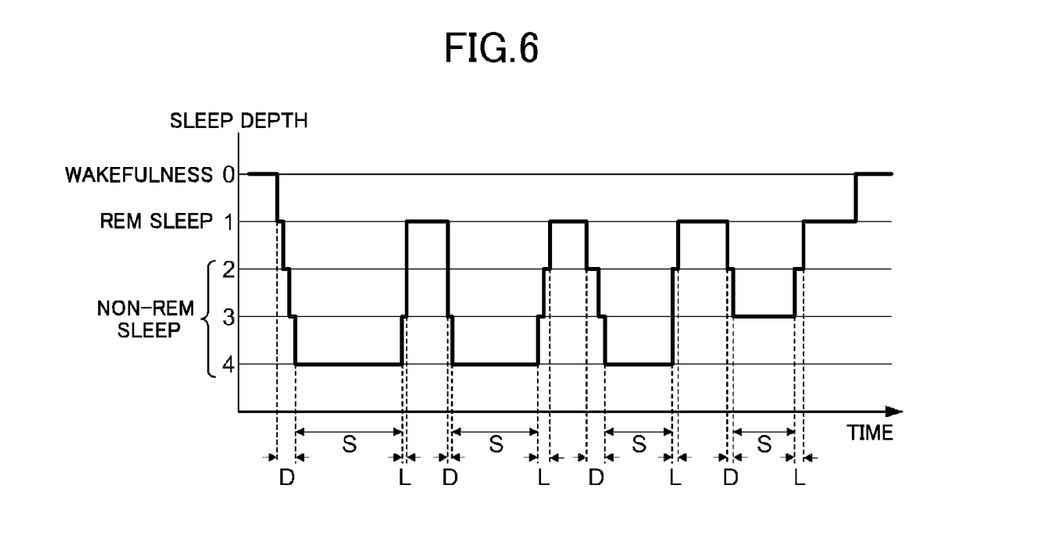
FIG. 6 is an example of a graph showing a variation with time of a sleep depth obtained by the sleep log data according to the embodiment.

The sleep depth data acquisition unit 112 stores the acquired sleep depth data in the storage unit 113 as the sleep log data along with data indicating a time of the acquisition. FIG. 5 is a table exemplifying a structure of the sleep log data. The sleep log data corresponding to one day (normally, one night) continuously stored in the storage unit 113 indicates a variation with time of the sleep depth corresponding to the one day of the user U as a whole. FIG. 6 is an example of a graph showing the variation with time of the sleep depth of the user U, which is indicated by the sleep log data corresponding to one day.

The vertical axis of FIG. 6 indicates the sleep depth, "0" represents wakefulness, "1" represents REM sleep, and "2" to "4" represent non-REM sleep. The horizontal axis of FIG. 6 indicates time. In FIG. 6, a period during which the sleep depth is "0" indicates a period (hereinafter referred to as "wakefulness stage") during which the user U is in a wakeful state, and a period during which the sleep depth is "1" indicates a period (hereinafter referred to as "REM sleep stage") during which the user U is in a REM sleep.

In this embodiment, the period during which the user U is in the non-REM sleep (period during which the sleep depth is "2" to "4") is classified into three kinds of a period D, a period S, and a period L. The period D is a period (hereinafter referred to as "deepened stage") during which the sleep depth is changing toward a deep level (being deepened), the period S is a period (hereinafter referred to as "stable stage") during which the sleep depth is stable, and the period L is a period (hereinafter referred to as "lightened stage") during which the sleep depth is changing toward a shallow level. The periods indicated by "D", "S", and "L" in FIG. 6 indicate periods of the deepened stage, the stable stage, and the lightened stage, respectively. However, the classification of the periods of the non-REM sleep is not limited to the above-mentioned three classes, and, for example, finer classification or broader classification may be employed.

The storage unit 113 stores the sound emission log data generated by the selection unit 111 and the sleep log data generated by the sleep depth data acquisition unit 112.

The sleep state identification unit 114 identifies the sleep state of the user U at a specific timing based on the sleep log data (indicating the variation with time of the sleep depth indicated by this deep depth data). Specifically, based on a pattern (for example, shape of the graph exemplified in FIG. 6) of the variation with time of the sleep depth of the user U indicated by the sleep log data, the sleep state identification unit 114 identifies the periods during which the sleep state of the user U is in each of the wakefulness stage, the REM sleep stage, the deepened stage, the stable stage, and the lightened stage and the sleep depth in the stable stage, and generates sleep state data indicating those identified sleep states. However, the type of sleep state of the user U to be identified by the sleep state identification unit 114 is not limited thereto, and the sleep state of, for example, another type such as the sleep depth in the REM sleep stage may be identified.

The generation unit 115 generates the influence data indicating an influence exerted on the sleep depth of the user U by the examination sound based on the sleep depth data. Specifically, the generation unit 115 generates the influence data based on the sleep state data indicating the sleep state identified by the sleep state identification unit 114 based on the sleep log data. Now, a description is made of a specific example of processing for generating the influence data performed by the generation unit 115.

In a state in which the storage unit 113 stores the sound emission log data corresponding to N days generated by the selection unit 111 during the period (hereinafter referred to as "examination period") of a predetermined number of days (hereinafter referred to as "2N days (N represents a predetermined natural number)") and the sleep log data corresponding to 2N days generated by the sleep depth data acquisition unit 112 during the same period, the generation unit 115 first identifies the non-sound emitting day and the examination sound emitting day based on the sound emission log data. Further, the generation unit 115 acquires the sleep state data indicating the sleep state of the user U during the examination period from the sleep state identification unit 114.

Figure 7:
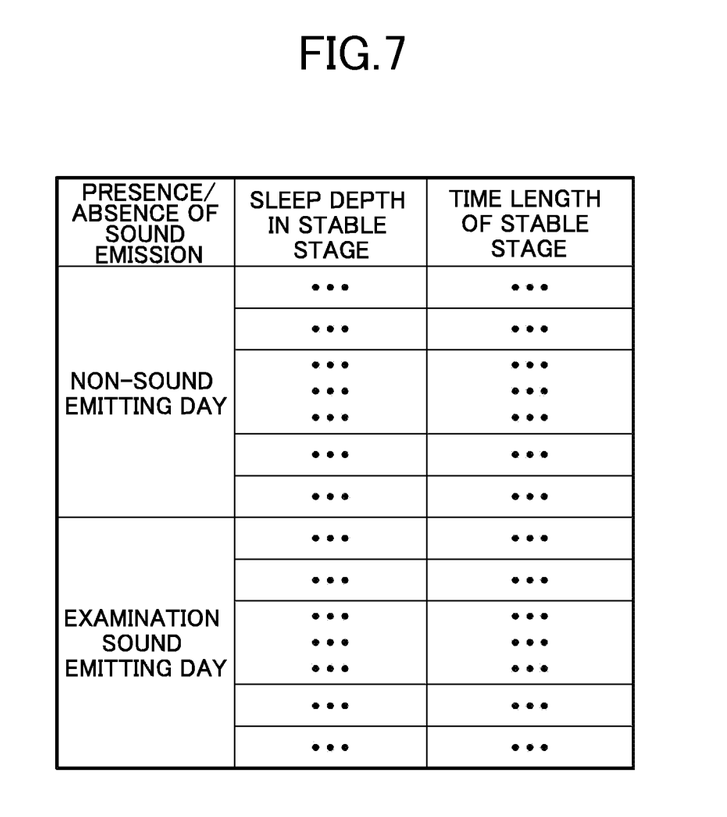
FIG. 7 is a table exemplifying a structure of a good sleep index according to the embodiment.

Subsequently, based on the sleep state data, the generation unit 115 generates an index (hereinafter referred to as "good sleep index") indicating a level of a degree of the good sleep of the user U. FIG. 7 is a table exemplifying a structure of the good sleep index generated by the generation unit 115. As shown in FIG. 7, the generation unit 115 classifies days within the examination period into the non-sound emitting day and the examination sound emitting day, and generates an index of the sleep depth of the user U in the stable stage on each day and an index of a time length of the stable stage. As a specific example, the index of the sleep depth in the stable stage is an average value of the sleep depth in the stable stage (for example, value obtained by weighted averaging a value of the sleep depth in each of stable stages (4 in the example of FIG. 6) by a weight corresponding to the time length of each stable stage), but the present invention is not limited thereto. For example, the index of the sleep depth may be generated based on the highest value or the lowest value of the stable stage. Further, as a specific example, the index of the time length in the stable stage is a total sum value of the time lengths in the stable stages (4 in the example of FIG. 6), but the present invention is not limited thereto.

Here, the good sleep index for each of the non-sound emitting day and the examination sound emitting day shown in FIG. 7, specifically, each of data on the index of the sleep depth in the stable stage and data on the index of the time length of the stable stage, can be grasped as sample data belonging to each of two different populations, in other words, a population for the non-sound emitting day and a population for the examination sound emitting day. Based on statistical values, for example, an average and variance (distribution), of the sample data on each of those two populations, the generation unit 115 tests a hypothesis as to whether or not there is a statistically significant difference regarding the good sleep index between those two populations. As a statistic method used by the generation unit 115 for the test, for example, any one of known statistic methods such as F test and t test may be employed. Based on results of the tests of the hypothesis, the generation unit 115 determines whether or not the examination sound is a sound that deepens the sleep depth in the stable stage of the user U (that is, sound that promotes the deepening of the sleep depth in the deepened stage) and whether or not the examination sound is a sound that maintains/continues the stable stage of the user U. Further, as a simpler method, for example, the generation unit 115 may be configured to calculate the average value of the sleep depth in the stable stage in regard to each of the sample data on the examination sound emitting day and the sample data on the non-sound emitting day, and when the average value regarding the examination sound emitting day is higher than the average value regarding the non-sound emitting day by at least a predetermined rate, determine that the examination sound is the sound that deepens the sleep depth in the stable stage of the user U. In the same manner, the generation unit 115 may be configured to calculate the average value of the time length of the stable stage in regard to each of the sample data on the examination sound emitting day and the sample data on the non-sound emitting day, and when the average value regarding the examination sound emitting day is higher than the average value regarding the non-sound emitting day by at least a predetermined rate, determine that the examination sound is the sound that maintains/continues the stable stage of the user U. The generation unit 115 generates the influence data indicating the results of the determination performed in the above-mentioned method. The influence data includes the deepening flag indicating whether or not the examination sound is the sound that promotes the deepening of the sleep depth in the deepened stage of the user U ("1" when promoting the deepening of the sleep depth, and otherwise "0") and the maintaining flag indicating whether or not the examination sound is the sound that maintains/continues the stable stage of the user U ("1" when increasing the time length, and otherwise "0"). The generation unit 115 stores the generated influence data in the sound DB shown in FIG. 2 along with the file name of the sound data on the examination sound. Note that, the sound data in which at least one of the deepening flag and the maintaining flag indicates "1" is the sound data indicating the good sleep sound for the user U.

1.2. Operation Mode

In the above-mentioned examination mode, when the influence data relating to at least one examination sound is stored in the sound DB shown in FIG. 2 by the generation unit 115, the user U is allowed to use the good sleep sound reproduction system 1 in the operation mode. The processor 101 of the good sleep sound reproduction device 11 performs the processing in accordance with the program for the operation mode stored in the memory 102, to thereby operate as a device including a functional configuration illustrated in FIG. 8. The good sleep sound reproduction device 11 in the operation mode includes all the functional components except the generation unit 115 of the functional components included in the examination mode. The processings performed by the sleep depth data acquisition unit 112 and the storage unit 113 in the operation mode are the same as the processing performed in the examination mode. On the other hand, in the operation mode, the processings performed by the selection unit 111 and the sleep state identification unit 114 are different from the corresponding processings performed in the examination mode.

Figure 8:
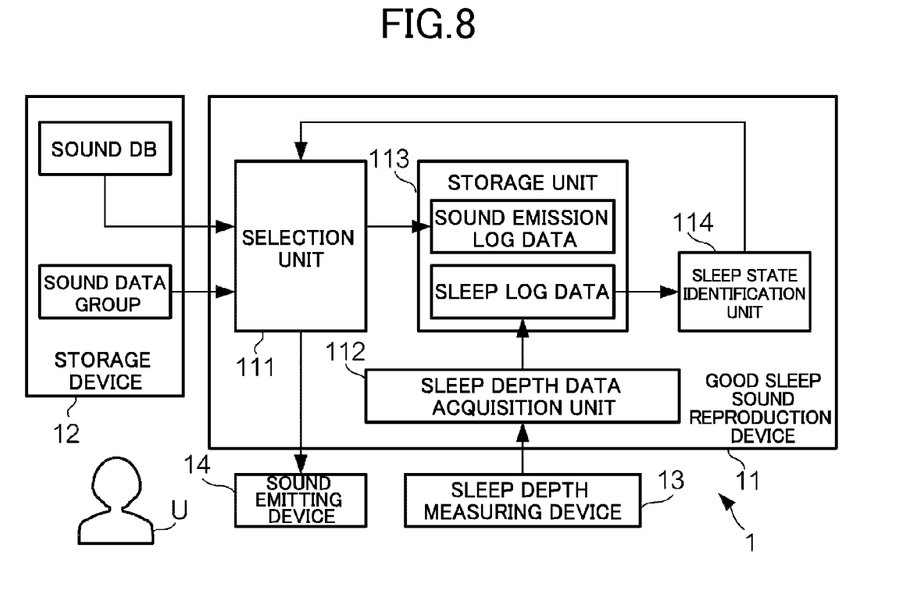
FIG. 8 is a block diagram for illustrating a functional configuration (operation mode) of the good sleep sound reproduction device according to the embodiment.

In the operation mode, the selection unit 111 selects the sound data corresponding to the current sleep state of the user U indicated by the sleep state data generated by the sleep state identification unit 114, as the sound data for sound emission, based on the influence data. Specifically, when the current sleep state of the user U is in the deepened stage, the selection unit 111 selects the sound data for sound emission from the sound data within the sound DB in which the value of the deepening flag is "1", for example, at random or in accordance with a predetermined rule. Further, when the current sleep state of the user U is in the stable stage, the selection unit 111 selects the sound data for sound emission from the sound data within the sound DB in which the value of the maintaining flag is "1", for example, at random or in accordance with a predetermined rule. The selection unit 111 repeatedly outputs the sound data for sound emission selected as described above to the sound emitting device 14 until the sleep state of the user U is changed, to thereby cause the sound emitting device 14 to perform the loop playback of the sound. When the current sleep state of the user U is not in the deepened stage or the stable stage, the selection unit 111 is inhibited from selecting or outputting the sound data.

In order to allow the selection unit 111 to perform the above-mentioned processing, in the operation mode, the sleep state identification unit 114 identifies the current sleep state of the user U in real time, and generates the sleep state data indicating the identified sleep state.

Now, a description is made of a specific example of processing performed by the sleep state identification unit 114 for identifying the current sleep state of the user U in real time and generating the sleep state data indicating the identified sleep state. After the current sleep depth of the user U indicated by the sleep depth data (acquired from the sleep depth measuring device 13 by the sleep depth data acquisition unit 112 each time a predetermined time period elapses) is changed toward the deep level, the sleep state identification unit 114 determines that the user U is in the deepened stage until the predetermined time period has elapsed, or until the sleep depth has reached the deepest level "4". Further, the sleep state identification unit 114 determines that the user U has entered the stable stage when there is no change for a predetermined time period after the sleep depth has reached "2" or "3", or when the sleep depth has reached the deepest level "4". Further, the sleep state identification unit 114 determines that the user U is in the lightened stage until a predetermined time period has elapsed after the sleep depth is changed toward the shallow level, or until the sleep depth has reached "1" indicating the REM sleep. Further, the sleep state identification unit 114 determines that the user U is in the REM sleep stage while the sleep depth is "1", and that the user U is in the wakefulness stage while the sleep depth is "0". The sleep state identification unit 114 generates the data indicating those results of the determination as the sleep state data indicating the current sleep state of the user U. The sleep state data generated by the sleep state identification unit 114 is passed over to the selection unit 111, and is used for the above-mentioned selection of the sound data.

Note that, as in the case of the examination mode, in the operation mode, the sound emission log data may be generated by the selection unit 111, or the sleep log data may be generated by the sleep depth data acquisition unit 112. When neither of the log data is generated, the storage unit 113 may be omitted. The sound emission log data and the sleep log data that are generated in the operation mode are stored in the storage unit 113, and become available in the following examination mode. Further, in the operation mode, the sleep state identification unit 114 may acquire the sleep depth data from the sleep log data, or may acquire the sleep depth data from the sleep depth data acquisition unit 112.

According to the good sleep sound reproduction system 1 described above, the good sleep sound for the user U is identified in the examination mode. Further, according to the good sleep sound reproduction system 1, the good sleep sound identified in the examination mode is emitted for the sleeping user U in the operation mode. In that case, the good sleep sound corresponding to the current sleep state of the user U is emitted. As a result, it is expected that the user U be guided to the good sleep compared to the case where the good sleep sound reproduction system 1 is not used.

2. Modification Examples

The above-mentioned embodiment is an embodiment of the present invention, and various modifications may be made within the scope of technical thought of the present invention. Modification examples thereof are described below.

2.1. First Modification Example

The good sleep sound reproduction system 1 according to a first modification example of the present invention records disturbance sounds (sounds of air conditioning, sounds of a refrigerator, sounds of falling rain, and the like) that are heard by the user U during his/her sleep, and uses the disturbance sound when the disturbance sound is the good sleep sound for the user U. Note that, in the drawings referred to in the description of this modification example, components that are common to or correspond to the components of the good sleep sound reproduction system 1 according to the above-mentioned embodiment are denoted by the same reference symbols.

Figure 9:
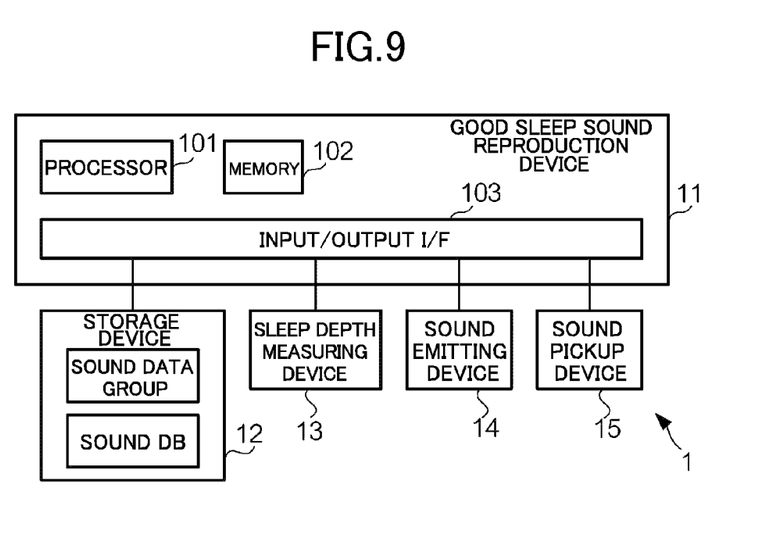
FIG. 9 is a block diagram illustrating a configuration of a good sleep sound reproduction system according to a modification example of the present invention.

FIG. 9 is a block diagram illustrating a configuration of the good sleep sound reproduction system 1 according to the first modification example. The good sleep sound reproduction system 1 according to the first modification example includes a sound pickup device 15 (sound collecting device) connected to the good sleep sound reproduction device 11 in addition to the components included in the good sleep sound reproduction system 1 according to the above-mentioned embodiment. The sound pickup device 15 is a known microphone, and picks up a sound within the space in which the user U is sleeping, generates the sound data indicating the above-mentioned sound, and outputs the sound data to the good sleep sound reproduction device 11. Note that, the sound pickup device 15 may be built into the good sleep sound reproduction device 11, or may be connected (connected in a wired manner or a wireless manner) as an external device.

Figure 10:
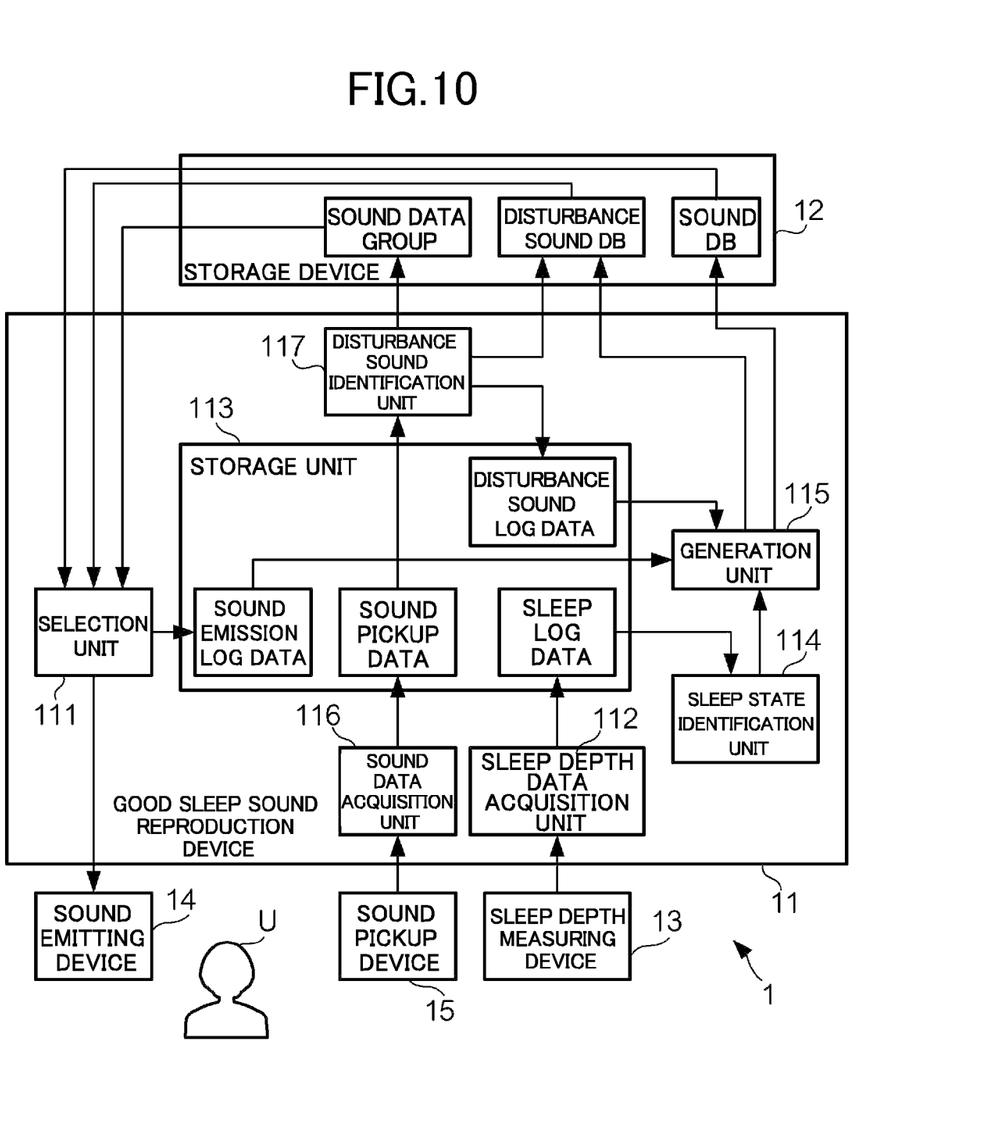
FIG. 10 is a block diagram for illustrating a functional configuration (examination mode) of a good sleep sound reproduction device according to the modification example.

FIG. 10 is a diagram illustrating a functional configuration of the good sleep sound reproduction device 11 in the examination mode according to the first modification example. In the examination mode, unlike the good sleep sound reproduction device 11 according to the above-mentioned embodiment, the good sleep sound reproduction system 1 according to the first modification example includes a sound data acquisition unit 116 for acquiring sound data from the sound pickup device 15 and storing the sound data in the storage unit 113 and a disturbance sound identification unit 117 for identifying a disturbance sound included in the sound indicated by the sound data stored in the storage unit 113.

The sound data acquisition unit 116 sequentially acquires the sound data (hereinafter referred to as "pickup sound data") continuously input from the sound pickup device 15, and stores the sound data in the storage unit 113. The pickup sound data mainly indicates the examination sound when the examination sound is being emitted from the sound emitting device 14, and indicates mostly silence when the examination sound is not being emitted from the sound emitting device 14. However, the sound indicated by the pickup sound data may include the disturbance sounds (sounds of air conditioning, sounds of a refrigerator, sounds of falling rain, sounds of the wind, and the like).

At a timing or the like at which, for example, the user U awakes and instructs the good sleep sound reproduction device 11 to stop the operation, the disturbance sound identification unit 117 first determines, based on the sound emission log data, whether or not the present day is the examination sound emitting day, and when the present day is the examination sound emitting day, identifies the emitted sound data for examination. The disturbance sound identification unit 117 cancels the examination sound included in the sound indicated by the pickup sound data relating to the examination sound emitting day by a known method by using the identified sound data for examination, and generates the pickup sound data indicating only the disturbance sound or mostly silence. The pickup sound data obtained by canceling the examination sound relating to the examination sound emitting day generated by the disturbance sound identification unit 117 is stored in the storage unit 113. With this configuration, the pickup sound data indicating the disturbance sound or mostly silence is stored in the storage unit 113 on both the non-sound emitting day and the examination sound emitting day. When the pickup sound data indicating only the disturbance sound or mostly silence is newly stored in the storage unit 113, the disturbance sound identification unit 117 determines whether or not the sound indicated by the sound data includes a disturbance sound by frequency analysis or the like, and identifies an acoustic characteristic of the disturbance sound when the disturbance sound is continuously included. Note that, in this modification example, it is assumed that the disturbance sound is distinguished in accordance with an acoustic characteristic thereof, and that two disturbance sounds whose similarity in the acoustic characteristic is higher than a predetermined threshold value are handled as the same disturbance sound.

Figure 11:
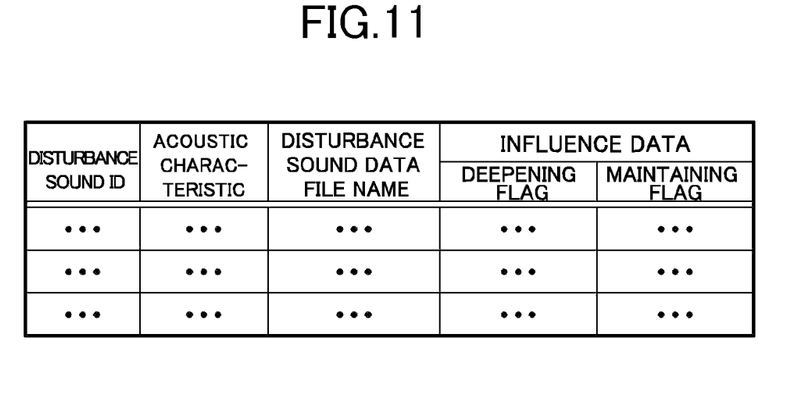
FIG. 11 is a table exemplifying a data structure of a disturbance sound DB according to the modification example.

When identifying the disturbance sound, the disturbance sound identification unit 117 stores the identification result in the storage device 12. Therefore, the storage device 12 stores a disturbance sound DB serving as a database for managing the disturbance sound. FIG. 11 is a table exemplifying a data structure of the disturbance sound DB. In association with a disturbance sound ID for identifying the disturbance sound, the disturbance sound DB stores the acoustic characteristic of the disturbance sound, a file name of the pickup sound data on the disturbance sound (disturbance sound data filename), and the influence data (deepening flag and maintaining flag) indicating an influence exerted on the sleeping user U by the disturbance sound.

When identifying a new disturbance sound, the disturbance sound identification unit 117 assigns the disturbance sound ID to the disturbance sound, and stores in the disturbance sound DB a new record formed of the assigned disturbance sound ID, data indicating the acoustic characteristic of the new disturbance sound, and the file name of the pickup sound data indicating a new disturbance sound.

Figure 12:
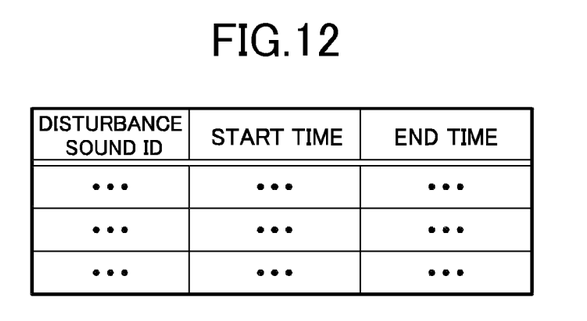
FIG. 12 is a table exemplifying a structure of disturbance sound log data according to the modification example.

Then, in association with the newly assigned disturbance sound ID, the disturbance sound identification unit 117 generates data indicating a start time and an end time of the disturbance sound, and stores the data in the storage unit 113 as the disturbance sound log data. FIG. 12 is a table exemplifying a structure of the disturbance sound log data.

The generation unit 115 determines whether or not at least a predetermined number of (hereinafter referred to as "M") pieces of disturbance sound log data relating to the disturbance sounds identified by the same disturbance sound ID are stored in the storage unit 113 at the timing or the like at which, for example, the user U instructs the good sleep sound reproduction device 11 to stop the operation. In regard to a given disturbance sound ID, when there are at least M pieces of disturbance sound log data, the generation unit 115 determines whether or not there is a statistically significant difference in the sleep depth between populations of two groups of sample data regarding the sleep log data corresponding to the periods indicated by those pieces of disturbance sound log data (sample data relating to the day when there is a disturbance sound corresponding to the disturbance sound ID) and the sleep log data corresponding to the period without a disturbance sound (period that does not overlap with the period indicated by the disturbance sound log data) (sample data relating to the day of mostly silence). Based on the result of the determination, the generation unit 115 generates the influence data (deepening flag and maintaining flag) relating to the disturbance sound corresponding to the disturbance sound ID. The processing performed by the generation unit 115 for generating the influence data relating to the disturbance sound is the same as the processing for generating the influence data relating to the examination sound. The generation unit 115 stores the generated influence data in the disturbance sound DB. The disturbance sound in which at least one of the deepening flag and the maintaining flag is "1" functions as the good sleep sound for the user U.

In the operation mode, in the same manner as the sound data registered in the sound DB, the sound data indicating the disturbance sound registered in the disturbance sound DB is selected by the selection unit 111 as the sound data indicating the good sleep sound, and is used for sound emission.

Note that, in the above-mentioned configuration according to this modification example, irrespective of whether the present day is the examination sound emitting day or the non-sound emitting day, the sleep log data relating to the period during which there is a disturbance sound and the sleep log data relating to the period during which there is no disturbance sound are handled as comparison subjects. Instead, for example, the sleep log data relating to the period during which there is a disturbance sound on the non-sound emitting day and the sleep log data relating to the period during which there is no disturbance sound on the non-sound emitting day may be handled as comparison subjects.

In addition, the sleep log data relating to the period during which there is a disturbance sound on the examination sound emitting day and the sleep log data relating to the period during which there is no disturbance sound on the examination sound emitting day may be handled as comparison subjects. In this case, instead of the configuration for registering the sound data including only the disturbance sound in the disturbance sound DB, the pickup sound data indicating the sound in which the examination sound and the disturbance sound are mixed may be registered in the disturbance sound DB as it is. This is because when the disturbance sound acts as the good sleep sound by being mixed with the examination sound, it is desired that the sound emitted in the operation mode be the sound in which the examination sound is not canceled.

Further, in this modification example, when the selection unit 111 selects the sound data for sound emission in the operation mode, the selection unit 111 may select the sound data from each of the sound DB and the disturbance sound DB, mix both, and then output the sound data to the sound emitting device 14.

2.2. Second Modification Example

In a second modification example of the present invention, in the same manner as in the above-mentioned first modification example, the good sleep sound reproduction system 1 includes the sound pickup device 15 connected to the good sleep sound reproduction device 11, and stores the pickup sound data acquired from the sound pickup device 15 by the good sleep sound reproduction device 11 in the examination mode in the storage unit 113. In the second modification example, in the generation of the influence data on each individual examination sound, the generation unit 115 generates an index (for example, average value of an S/N ratio) indicating a degree to which a disturbance sound is included in the sound indicated by the pickup sound data when the examination sound is emitted (hereinafter referred to as "noise index"), and stores the index in the sound DB along with the influence data.

In the operation mode, when selecting the sound data for sound emission, the selection unit 111 preferentially selects a disturbance sound that is small at a time of examination based on the noise index from among a plurality of pieces of sound data on the good sleep sound stored in the sound DB. For example, when the S/N ratio (ratio of the level of the examination sound to the level of the disturbance sound) is used as the noise index, the selection unit 111 is more likely to select the sound data whose S/N ratio is larger at the time of examination from among the pieces of sound data indicating the good sleep sound. Alternatively, the selection unit 111 increases a time period for outputting to the sound emitting device 14 with regard to the sound data whose S/N ratio is larger at the time of examination.

According to this modification example, a sound in which the influence of the disturbance sound is small at the time of examination, and in which the determination as to whether or not the sound is a good sleep sound is highly reliable, is preferentially emitted. As a result, even when the disturbance sound at the time of examination is a good sleep sound and when the examination sound is erroneously determined as a good sleep sound even though the examination sound is not a good sleep sound, the sound erroneously determined as a good sleep sound is emitted in the operation mode with low probability, which prevents the effect of the good sleep sound reproduction system 1 from deteriorating.

2.3. Third Modification Example

In the above-mentioned embodiment, in the operation mode, the good sleep sound reproduction system 1 emits the good sleep sound while the user U is sleeping. Therefore, the user U cannot know what kind of sound is the good sleep sound for himself/herself. The above-mentioned embodiment may be modified so that the user U can know the good sleep sound for himself/herself (third modification example of the present invention). In the third modification example, the good sleep sound reproduction system 1 includes a display device (which is any one of internally and externally) connected to the good sleep sound reproduction device 11, and the display device displays a list of good sleep sounds (for example, list of the file names of the sound data). For example, when the user U operates a user interface of the good sleep sound reproduction device 11 to select the desired sleep sound from the list displayed on the display device, the sound data on the selected good sleep sound is output from the storage device 12 to the sound emitting device 14 via the good sleep sound reproduction device 11, and the good sleep sound selected by the user U is emitted from the sound emitting device 14. As a result, the user U can know what kind of sound is a good sleep sound for himself/herself.

2.4. Fourth Modification Example

A fourth modification example of the present invention provides a good sleep sound information providing system for providing various services using data relating to the good sleep sounds for a plurality of users in a state in which the plurality of users use their own good sleep sound reproduction systems 1.

Figure 13:
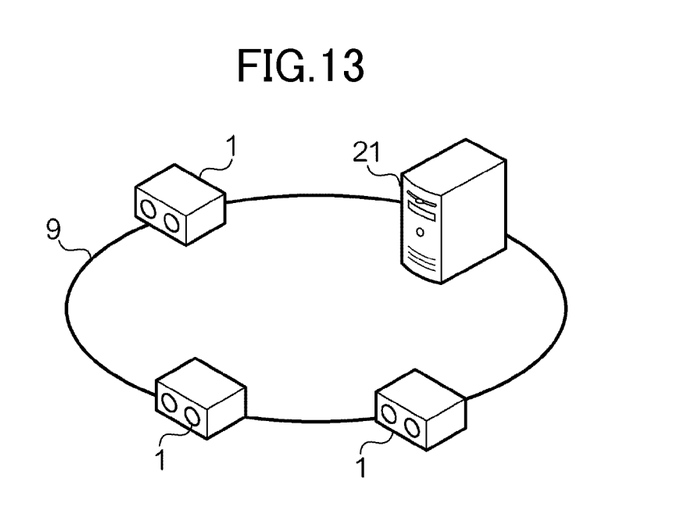
FIG. 13 is a diagram illustrating a configuration of a good sleep sound information providing system according to another modification example of the present invention.

FIG. 13 is a diagram illustrating a configuration of the good sleep sound information providing system according to this modification example. The good sleep sound information providing system includes a plurality of good sleep sound reproduction systems 1 and a server device 21. The respective good sleep sound reproduction systems 1 are used by different users. Note that, FIG. 13 illustrates an example of three good sleep sound reproduction systems 1, but the number of good sleep sound reproduction systems 1 included in the good sleep sound information providing system changes depending on the number of users who use the good sleep sound information providing system.

The good sleep sound reproduction device 11 of the good sleep sound reproduction system 1 included in the good sleep sound information providing system includes a communication unit for performing data communications to/from the server device 21. The good sleep sound reproduction device 11 uploads the sound DB shown in FIG. 2 stored in the storage device 12, the sound data referred by the sound data file name stored in the sound DB, and the sleep log data shown in FIG. 5 stored in the storage unit 113, onto the server device 21 via a network 9. Note that, the data uploaded onto the server device 21 by the good sleep sound reproduction device 11 may be only a difference between data already stored on the server device 21 and data stored on the storage device 12 and the storage unit 113. Further, a timing at which the good sleep sound reproduction device 11 uploads the data onto the server device 21 may be any timing such as a timing at which, for example, the sound DB and the sleep log data are updated or a timing at which a predetermined time period has elapsed.

The server device 21 manages the sound DB and the sound data uploaded from each of the plurality of good sleep sound reproduction devices 11 for each user, and transmits at least a part of the sound DB on a given user, the sound data, and the sleep log data to the good sleep sound reproduction device 11 at a request source in response to a request received from the good sleep sound reproduction device 11 of the given user. That is, the server device 21 is used as an external storage device of the good sleep sound reproduction device 11. Therefore, when the server device 21 is accessible via the network 9, instead of the sound DB, the sound data group, and the sleep log data stored in the storage device 12, the good sleep sound reproduction device 11 may use those pieces of data stored on the server device 21.

Further, the server device 21 includes, for example, a web server function, and provides users with various services using at least a part of the sound DBs, the sound data group, and the sleep log data on the plurality of users. The good sleep sound reproduction device 11 includes, for example, a web browser function, and the user accesses an information site provided by the server device 21 through the web browser executed on the good sleep sound reproduction device 11, and receives provision of the various services by the server device 21. Now, a description is made of an example of the service provided to the user by the server device 21.

(Good Sleep Sound Matching Function)

This is a function of notifying the requesting user of another user for whom the good sleep sound is similar. The server device 21 compares the sound DB of the requesting user with the sound DB of another user, and calculates a concordance rate of the influence data (deepening flag and maintaining flag) relating to the same sound data (whose sound data file names match) as a similarity of the good sleep sound. The server device 21 transmits a web page in which, for example, the list of names (for example, handles) of a predetermined number of users is displayed in decreasing order of the similarity of the good sleep sound, to the good sleep sound reproduction device 11 of the requesting user.

Note that, a rule based on which the server device 21 calculates the similarity of the good sleep sound may be modified variously. For example, instead of the same sound data, a rule for calculating the similarity of the good sleep sound to become higher may be employed when the influence data matches in regard to the sound data indicating the sound whose tone, rhythm, and the like are similar.

(Sleep Pattern Matching Function)

This is a function of notifying the requesting user of another user for whom the change pattern of the sleep depth is similar. The server device 21 compares the sleep log data of the requesting user with the sleep log data of another user, and calculates the similarity of a pattern shown in FIG. 6 of the variation with time of the sleep depth indicated by each of those pieces of sleep log data. The server device 21 transmits a web page in which, for example, the list of names (for example, handles) of a predetermined number of users is displayed in decreasing order of the similarity of the pattern of the variation with time of the sleep depth, to the good sleep sound reproduction device 11 of the requesting user.

(Good Sleep Sound Update Function)

This is a function of distributing the sound DB and the sound data of another user designated by the requesting user to the good sleep sound reproduction device 11 of the user. When the name (for example, handle) of another user is designated by the requesting user, the server device 21 extracts the data record in which the influence data is unregistered in the sound DB of the requesting user and the deepening flag or the maintaining flag for the influence data is "1" in the sound DB of the user having the designated name, and transmits the data record to the good sleep sound reproduction device 11 of the requesting user.

Further, when the sound data file name is designated by the requesting user along with the name (for example, handle) of another user, the server device 21 searches the sound DB of the user having the designated name for a data record by using the designated sound data file name as a search key, and transmits the data record to the good sleep sound reproduction device 11 of the requesting user.

Note that, in regard to the sound data file that is not registered in the sound DB of the requesting user among the sound data files indicated by the data record to be transmitted to the good sleep sound reproduction device 11 of the requesting user, the server device 21 transmits the sound data corresponding to those sound data file names to the good sleep sound reproduction device 11 of the requesting user.

The good sleep sound reproduction device 11 of the requesting user updates the sound DB stored in the storage device 12 by using the data record of the sound DB transmitted from the server device 21. Further, the good sleep sound reproduction device 11 of the requesting user adds the sound data transmitted from the server device 21 to the sound data group stored in the storage device 12.

According to this function, for example, the user is allowed to know another user for whom the good sleep sound or the change pattern of the sleep depth is similar to that of the user himself/herself by using the good sleep sound matching function or the sleep pattern matching function, and then to use all the good sleep sounds of the another user or the good sleep sound designated from among the good sleep sounds of the another user as the user's own good sleep sound. In this manner, the influence data on another person similar to himself/herself in the characteristic of sleep can be used to increase the registration of the good sleep sounds without undergoing the examination mode.

(Communication Assisting Function)

This is a function of assisting communications among a plurality of users. When receiving a message directed to another user from the good sleep sound reproduction device 11 of a given user, the server device 21 distributes the message to the good sleep sound reproduction device 11 of the user of the destination.

According to this function, for example, the user is allowed to know another user for whom the good sleep sound or the change pattern of the sleep depth is similar to that of the user himself/herself by using the good sleep sound matching function or the sleep pattern matching function, and then to send a message to the another user, to thereby come to know a person to be a good match for the user himself/herself in terms of sleep. For example, if a couple who came to know each other by using this function gets married, the couple can live a healthy marriage without disturbing each other's sleep.

Note that, in the above-mentioned good sleep sound information providing system, the server device 21 stores the sound DB, the sound data, and the sleep log data, but the data stored on the server device 21 and used for the services provided by the server device 21 is not limited to those pieces of the data. For example, data relating to other kinds of sleep such as the sound emission log data shown in FIG. 4 may be uploaded from the good sleep sound reproduction device 11 to the server device 21, and may be used for the services provided by the server device 21.

2.5. Other Modification Examples

In the above-mentioned embodiment, the good sleep sound reproduction device 11 identifies the sound that deepens the sleep depth in the deepened stage as the good sleep sound for the deepened stage, and identifies the sound that maintains the sleep depth in the stable stage as the good sleep sound for the stable stage. The mode in which the good sleep sound reproduction device 11 identifies the good sleep sound is not limited thereto, and various other modes can be employed. For example, it is conceivable to provide a mode in which data indicating a desired variation with time of the sleep depth (model pattern) is previously stored in the storage unit 113 of the good sleep sound reproduction device 11 or the storage device 12, and a sound for which a similarity (correlation coefficient or the like) between a pattern (for example, shape of the graph exemplified in FIG. 6) of the variation with time of the sleep depth of the user U indicated by the sleep log data on the examination sound emitting day and the model pattern is statistically recognized as higher than a similarity between a pattern of the variation with time of the sleep depth of the user U on the non-sound emitting day and the model pattern is identified as the good sleep sound. Further, it is conceivable to provide a mode for identifying the good sleep sound for the user U based on subjective determination of the user U. Specifically, for example, the user U may input data indicating comfort felt at the awaking to the good sleep sound reproduction device 11, and based on the data, a sound that is statistically recognized to improve the comfort felt when the user U awakes may be identified as the good sleep sound.

Further, in the above-mentioned embodiment, the good sleep sound reproduction device 11 alternately provides the non-sound emitting day and the examination sound emitting day, and uses the sleep depth data indicating the sleep depth of the user U on the non-sound emitting day as the sleep depth data serving as a reference (hereinafter referred to as "reference sleep depth data"), to thereby identify the influence exerted on the sleep depth of the user U by the examination sound. That is, the good sleep sound reproduction device 11 identifies the influence exerted on the sleep depth of the user U by the examination sound based on the variation with time of the sleep depth indicated by the sleep depth data indicating the sleep depth of the user U on the examination sound emitting day, that is, the sleep depth data (hereinafter referred to as "target sleep depth data") indicating the sleep depth of the user U in a state in which the examination sound (sound subjected to examination) is being emitted, and the variation with time of the sleep depth indicated by the reference sleep depth data. The method of acquiring the reference sleep depth data by the good sleep sound reproduction device 11 is not limited to the method according to the above-mentioned embodiment.

For example, prior to the emitting of the examination sound, the good sleep sound reproduction device 11 acquires the sleep log data including, as the reference sleep depth data, the sleep depth data indicating the sleep depth of the user U measured by the sleep depth measuring device 13 or another sleep meter in a state in which the examination sound is not being emitted, and stores the sleep log data in the storage unit 113. After that, without providing the non-sound emitting day in the examination mode, the good sleep sound reproduction device 11 causes the sound emitting device 14 to emit the examination sound, and at the same time, acquires the sleep depth data indicating the sleep depth of the user U measured by the sleep depth measuring device 13 as the target sleep depth data, and stores the sleep log data including the acquired target sleep depth data in the storage unit 113. After that, based on the variation with time of the sleep depth indicated by the sleep log data including the reference sleep depth data stored in the storage unit 113 and the variation with time of the sleep depth indicated by the sleep log data including the target sleep depth data, the good sleep sound reproduction device 11 identifies the influence exerted on the sleep depth of the user U by the examination sound, and generates the influence data indicating the identified influence.

As in the above-mentioned example, the reference sleep depth data used by the good sleep sound reproduction device 11 is not limited to the one acquired by the good sleep sound reproduction device 11 in the examination mode, and any sleep depth data may be used as long as the sleep depth data is the sleep depth data on the same user that can be used as a reference to the target sleep depth data acquired by the good sleep sound reproduction device 11 in the examination mode.

Note that, the reference sleep depth data is not limited to the sleep depth data indicating the sleep depth of the user U measured in a silent state or in a state in which the disturbance sound (such as sounds of air conditioning) is being emitted, and, for example, the sleep depth data indicating the sleep depth of the user U measured in the state in which a predetermined background sound (sound different from the examination sound) such as sounds of rippling waves is being emitted may be used as the reference sleep depth data.

Further, in the above-mentioned embodiment, the generation unit 115 of the good sleep sound reproduction device 11 determines whether or not a given sound is a good sleep sound for the user U, but does not determine the degree to which the good sleep sound guides the user U to a good sleep. Instead, the degree to which the good sleep sound guides the user U to a good sleep may be determined by the generation unit 115, and the influence data (which indicates a level of the degree of guiding to a good sleep by, for example, numerical values of "1" to "5") indicating the result of the determination may be generated. In this case, for example, in the operation mode, the selection unit 111 may preferentially select the sound data on the good sleep sound whose degree of guiding to a good sleep is high, and may output the sound data to the sound emitting device 14.

Further, in the above-mentioned embodiment, the sleep state based on which the generation unit 115 identifies the good sleep sound is not limited to the deepened stage or the stable stage, and the sleep state based on which the selection unit 111 selects the sound data on the good sleep sound is not limited to the deepened stage or the stable stage. For example, in the examination mode, in the lightened stage in the non-REM sleep or a transitioning state from the REM sleep stage to the wakefulness stage, the generation unit 115 may identify the sound that guides the sleep depth toward the shallow level as the good sleep sound corresponding to those sleep states. Further, in this case, it is possible to employ a configuration in which, in the operation mode, the selection unit 111 selects the sound data on the good sleep sound identified by the generation unit 115 as the sound data corresponding to those sleep states in the lightened stage in the non-REM sleep or the transitioning state from the REM sleep stage to the wakefulness stage.

Further, in the above-mentioned embodiment, the good sleep sound reproduction device 11 may include a function of an alarm clock. In this case, the storage unit 113 of the good sleep sound reproduction device 11 or the storage device 12 previously stores the data indicating the variation with time (model pattern) of the desired sleep depth. When the user U sets a wake-up time in the good sleep sound reproduction device 11, the selection unit 111 of the good sleep sound reproduction device 11 selects the good sleep sound and outputs the good sleep sound to the sound emitting device 14 so that the current sleep state of the user U indicated by the sleep depth data becomes closer to the model pattern that expands/contracts in a time axis direction so as to become wakeful at the wake-up time. When the wake-up time is reached, the selection unit 111 causes the sound emitting device 14 to emit a so-called alarm sound, to thereby wake up the user U. According to this modification example, it is expected that the comfort felt by the user U increase when awaking in response to the alarm sound.

Further, in the above-mentioned embodiment, a function of detecting a divergence when the good sleep sound identified by the good sleep sound reproduction device 11 in the examination mode in the past diverges from an actual situation may be provided. Note that, as an example in which the good sleep sound diverges from the actual situation, it is conceivable that, for example, a change occurs in a reaction of the user U against the sound or the disturbance sound is changed due to moving of the user U. The good sleep sound reproduction device 11 calculates the index (such as the sleep depth in the stable stage or the time length of the stable stage) indicating the degree of the good sleep of the user U based on the sleep log data in regard to, for example, each of the most recent sleeps within a predetermined period (or corresponding to a predetermined number of times) in the past. When the calculated index indicates that the degree of the good sleep deteriorates, the good sleep sound reproduction device 11 prompts the user U to start the examination mode by, for example, flashing an indicator or the like. In response to this prompt, when the user U instructs the good sleep sound reproduction device 11 to start the operation for the examination mode, the good sleep sound reproduction device 11 again executes the processing for the examination mode, and updates the sound DB.

Further, in the above-mentioned embodiment, even the same sound data pieces that are different in volume when being emitted from the sound emitting device 14 may be handled as different sounds.

Further, in the above-mentioned embodiment, the good sleep sound reproduction device 11 performs the processing in accordance with the programs stored in the memory 102 by the processor 101, to thereby function as a device including the components illustrated in FIG. 3 (examination mode) or FIG. 8 (operation mode). Instead, for example, the good sleep sound reproduction device 11 may be configured as a device including each of the components illustrated in FIG. 3 (examination mode) or FIG. 8 (operation mode) as hardware.

Note that, data structures, sequences and timings of the processing, conditions for the determination, and the like described in the above-mentioned embodiment are merely examples, and do not limit the present invention.

While there have been described what are at present considered to be certain embodiments of the invention, it will be understood that various modifications may be made thereto, and it is intended that the appended claims cover all such modifications as fall within the true spirit and scope of the invention.

What is claimed is:

1. A device, comprising:
   at least one processor;
   at least one memory device that stores a plurality of instructions, which when executed by the at least one processor, causes the at least one processor to:
   acquire sleep depth data indicating a sleep depth of a user in a state in which a sound is being emitted;
   generate a plurality of pieces of influence data indicating an influence exerted on a variation with time of the sleep depth of the user by the sound based on a variation with time of the sleep depth indicated by the acquired sleep depth data and a variation with time of the sleep depth serving as a reference relating to the user;
   store the plurality of pieces of the influence data;
   acquire sleep state data indicating a current sleep state of the user;
   select at least one piece of sound data from among a plurality of pieces of sound data based on the sleep state data and the plurality of pieces of the influence data that are respectively associated with the plurality of pieces of sound data that indicates a plurality of pieces of sound; and
   output the selected sound data to a sound emitting device.

2. The device according to claim 1, wherein the influence data indicates whether or not the sound is a sound that maintains the sleep depth of the user or a sound that deepens the sleep depth of the user.

3. The device according to claim 1, wherein:
the influence data indicates whether or not the sound is a sound that deepens the sleep depth of the user; and
the at least one processor further selects, when the sleep state data indicates a state in which the sleep depth is changing toward a deep level, at least one piece of sound data associated with the influence data indicating an influence that deepens the sleep depth among the plurality of pieces of the influence data.

4. The device according to claim 1, wherein:
the influence data indicates whether or not the sound is a sound that maintains the sleep depth of the user; and
the at least one processor further selects, when the sleep state data indicates a state in which the sleep depth is stable, at least one piece of sound data associated with the influence data indicating an influence that maintains stability of the sleep depth among the plurality of pieces of the influence data.

5. A non-transitory computer-readable storage medium storing a program configured to be executed by a processor comprising instructions for:

acquiring sleep depth data indicating a sleep depth of a user in a state in which a sound is being emitted;
generating a plurality of pieces of influence data indicating an influence exerted on a variation with time of the sleep depth of the user by the sound based on a variation with time of the sleep depth indicated by the sleep depth data and a variation with time of the sleep depth serving as a reference relating to the user;
storing the plurality of pieces of the influence data;
acquiring sleep state data indicating a current sleep state of the user;
selecting at least one piece of sound data from among a plurality of pieces of sound data based on the sleep state data and the plurality of pieces of the influence data that are respectively associated with the plurality of pieces of sound data that indicates a plurality of pieces of sound; and
outputting the selected sound data to a sound emitting device.

\* \* \* \* \*